United States Patent [19]

Muller et al.

[11] Patent Number: 5,152,761
[45] Date of Patent: Oct. 6, 1992

[54] PROCESS AND DEVICE FOR PROTECTING THE PROXIMAL LAUNCH SIDES OF LASER CATHETERS

[75] Inventors: Gerhard Muller; Hasan Kar; Klas Dorschel, all of Berlin; Karl-Heinz Schonborn, Mainz, all of Fed. Rep. of Germany

[73] Assignee: Schott Glaswerke, Mainz, Fed. Rep. of Germany

[21] Appl. No.: 494,745

[22] Filed: Mar. 19, 1990

[30] Foreign Application Priority Data

Mar. 17, 1989 [DE] Fed. Rep. of Germany ... 8903333[U]

[51] Int. Cl.⁵ .............................................. A61N 5/00
[52] U.S. Cl. ....................................... 606/16; 606/2; 606/15; 128/398; 385/81; 385/84; 385/88
[58] Field of Search .................. 606/2, 7, 10, 13–17; 128/395, 398; 350/96.2, 96.22

[56] References Cited

U.S. PATENT DOCUMENTS

| | | | |
|---|---|---|---|
| 4,209,227 | 6/1980 | Dubos et al. | 350/96.22 |
| 4,652,288 | 3/1987 | Saito | 65/3.11 |
| 4,698,084 | 10/1987 | Severijns et al. | 65/3.11 |
| 4,770,486 | 9/1988 | Wang et al. | 350/96.20 |
| 4,913,523 | 4/1990 | Yoshida et al. | 350/96.2 |
| 4,986,622 | 1/1991 | Martinez | 350/96.15 |

FOREIGN PATENT DOCUMENTS

| | | |
|---|---|---|
| 57-17903 | 1/1982 | Japan. |
| 61-208008 | 9/1986 | Japan. |
| 61-46734 | 11/1986 | Japan. |

*Primary Examiner*—David M. Shay
*Attorney, Agent, or Firm*—Millen, White & Zelano

[57] ABSTRACT

To protect the launch surfaces of laser catheters fed with short-pulsed laser radiation, the individual optical fibers are placed on the launch side in hexagonally closest packing. Ablation-resistant materials are applied to the outer circumference of the cross-section area adjacent to the launch device, and the individual fibers and the ablation-resistant materials are connected to one another by material or friction connections. The ablation-resistant materials are of the same material, silicate, or PTFE, as the optical fibers.

14 Claims, 2 Drawing Sheets

PROCESS AND DEVICE FOR PROTECTING THE PROXIMAL LAUNCH SIDES OF LASER CATHETERS

BACKGROUND OF THE INVENTION

The present invention relates to a process for shielding the launch ends of laser catheters used in photoablation of deposits in the vascular systems of the human body.

Laser catheters used in the medical field to recanalize clogged arteries have specific requirements. For example, load capacity and durability of the system must be able to accommodate associated threshold luminations. Launching of high energy, pulsed laser radiation at the proximal end of the catheter is an especially weak point in such systems system, often self-destructing under usual operating conditions, thereby curtailing the service life of the device.

For purposes of photoablation, launch side luminations of 20 J/cm$^2$ are necessary. Short, high-energy laser pulses in one or more optical fibers must be launched in the spectral range between 240-3000 nm. The threshold luminations required for photoablation to recanalize vessels, especially in the case of calcified occlusions, must be high enough to ablate organic material.

The launching surface of a single or multifiber laser catheter can change due to unavoidable movement of the laser beam. It is not possible to completely eliminate irradiation over the effective cross-section of the fiber or fiber bundle at the front sides of the launch surface In addition, the cross-section of the beam cannot be adapted easily to the cross-section of a multifiber catheter, causing unavoidable partial irradiation.

The materials used to hold the light fibers according to the prior art do not withstand incident lumination, resulting in ablation of the holding material at the launch side and early destruction of the catheter. For example, ablation of metal holding material leads to metal particle deposits on the launch surface of the fibers, indirectly causing destruction of the fiber. The use of standard plastics as holding materials does not overcome the shortcomings of the prior art because decomposition products of the plastic are deposited on the fiber end surface, resulting in loss of the setting and fiber destruction. Such deterioration poses significant risk to successful recanalization.

SUMMARY OF THE INVENTION

The object of the invention, therefore, is to provide a device and process for protecting the launch side portions of laser catheters in order to considerably increase the service life of the laser catheters.

There are several possibilities for modifying launching devices at the proximal end by using physical and/or laser light resistant binders. Quartz/quartz fibers in multifiber ring catheters are placed at the launch site to maximize geometric coupling efficiency in hexagonally closest packing arrangements. Laser light is launched into the multifiber ring catheter via connectors. In most cases, a metal sleeve in which the optical fibers are embedded by material and/or frictional connection can be used as a connector base, freeing the optical fibers of plastic cladding at the joining site.

In accordance with one approach, the quartz/quartz fibers are heated under axial traction and in hexagonally closest packing in a thin quartz tube to the softening temperature in order to fuse them together. The bundle is then separated in the middle of the fusion site, and the front side is optically polished. In this way, the fused-together quartz end section has the same optical properties for all individual fibers and can be received in a simple way in a metal sleeve which serves as a connector.

In accordance with a second approach, the fiber bundles are shrunk thermally in hexagonally closest packing in a metal holder made preferably of aluminum. To protect the metal surface, it is coated with either polymethylsiloxane (silicon rubber) or a silicate. In a preferred embodiment, the fiber bundle projects about 1 mm beyond the front end of the metal holder.

In an additional approach, the quartz/quartz fibers of a multifiber ring catheter are embedded in hexagonally closest packing by using a silicate as a joining means in a metal sleeve. In this arrangement, in a preferred embodiment, sodium hydrosilicate (water glass) is used. In this arrangement, the projecting fiber bundle is also separated at the edge position with the connector and the end surface optically polished.

A significant increase in service life surprisingly is attained when the holder of fibers in the active beam area is made by using polytetrafluoroethylene (PTFE). This material has a good ablation strength in the UV wavelength range of 300 to 350 nm which is especially critical for medical uses. The PTFE holders are also received in metal sleeves. In the case of multifiber ring catheters, individual fibers are held together in hexagonally closest packing by a PTFE heat-shrinkable sleeve, while the enlargement of the front side ablation-resistant cross-section takes place by PTFE fitted parts in the shape of a ring.

If the PTFE heat-shrinkable sleeve extends to the launch surface of the fiber bundle, laser radiation can cause the PTFE to creep over the end surfaces of the fiber bundle and thus interfere with the laser light launching. This can be avoided if the fiber ends are not completely surrounded by a PTFE heat-shrinkable sleeve up to the launch surface so that the fibers are free for a sufficient length. But if this is the case, the free fiber bundle cannot be optically polished subsequently on its front side. This drawback can be avoided if an outside layer of short fiber pieces, not used for transmission, is also shrunk with the bundle. In this case, the heat-shrinkable sleeve can reach to the fiber end, and achieves sufficient mechanical stability that subsequent polishing of the end surface of the total fiber bundle is possible.

BRIEF DESCRIPTION OF THE DRAWINGS

Preferred embodiments of the devices according to the invention for the launching side end of a laser catheter are explained below in even more detail with the help of the accompanying diagrammatic drawings, wherein.

DETAILED DESCRIPTION

Figure 1:
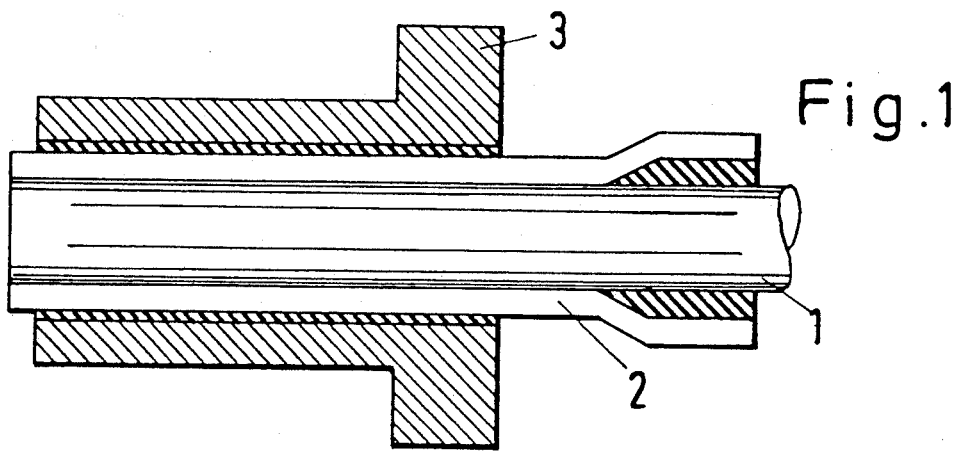
FIG. 1 is a diagrammatic longitudinal section through a launch connector in which the optical fibers are received in a thin quartz tube and fused with the tube.

In FIG. 1, a longitudinal section of a launch connector is illustrated. The quartz/quartz fiber bundles in hexagonally closest packing 1 are received in a quartz tube 2, which in turn is secured in a metal sleeve 3. The material between the quartz tube 2 and metal sleeve 3 is comprised, for example, of silicon resin or may be the end portion of a plastic cladding.

Figure 2:
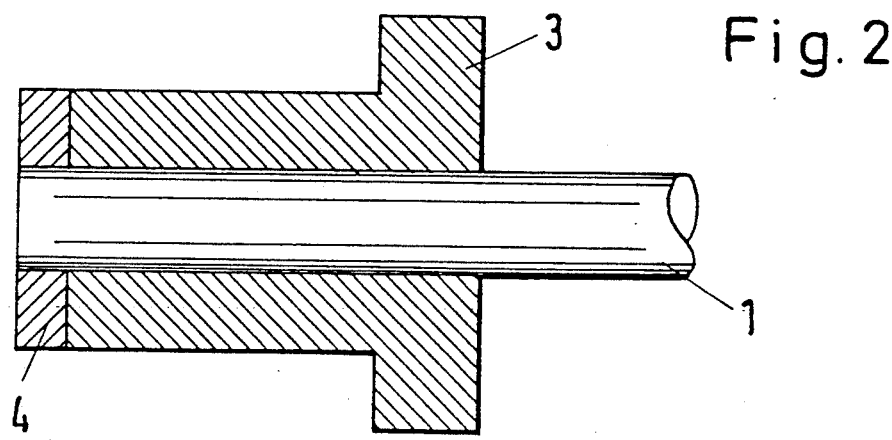
FIG. 2 is a diagrammatic longitudinal section through a launch connector in which a fiber bundle is thermally shrunk in a metal sleeve coated on the lead in side.

A second embodiment for a launch connector is shown in FIG. 2, where optical fibers 1, held in hexagonally closest packing, are shrunk directly in a metal sleeve 3, which is preferably made of aluminum. For protection from laser light, the metal sleeve 3 is coated at the lead-in end with a protective coating 4, preferably of polymethylsiloxane or silicate.

Figure 3:
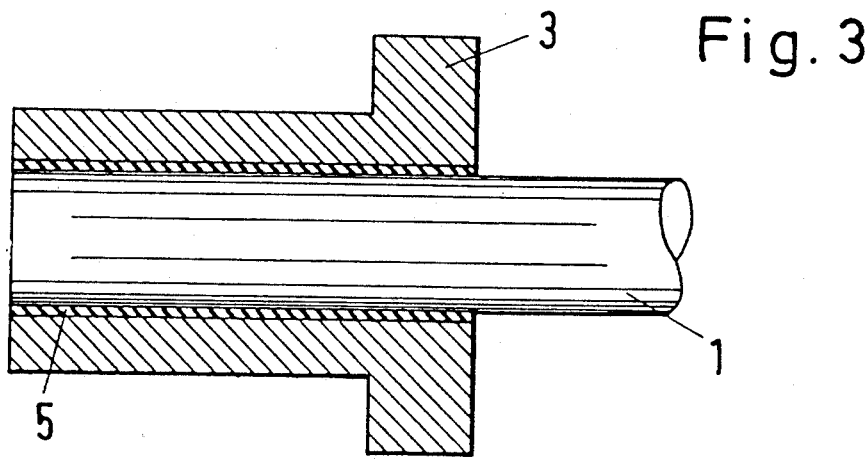
FIG. 3 is a diagrammatic longitudinal section through a launch connector in which optical fiber bundles are embedded in a metal sleeve with silicate adhesive.

In a third embodiment, as shown in FIG. 3, the hexagonally closest packing of optical fibers 1 is anchored in a silicate bed 5 in metal holder 3 so that on the lead-in surface, the cross-section area of the fiber optic light guide bundle insensitive to the laser light is enlarged by the front surface of silicate bed 5.

Figure 4:
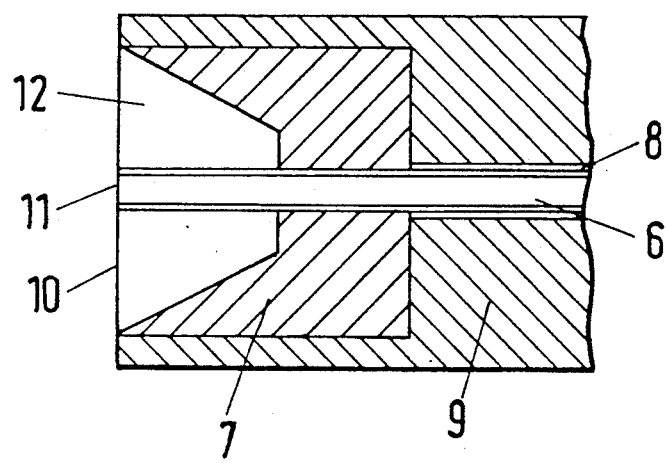
FIG. 4 is a diagrammatic longitudinal section through a launch connector, in which a quartz/quartz fiber in the active beam area is molded in a PTFE part, which, in turn, is anchored in a metal sleeve.

In FIG. 4, the holder of an individual quartz/quartz fiber 6 in a connector inner part is shown in longitudinal section. Quartz/quartz fiber 6 at the launch side end of the connector is held by a PTFE part in a bore, and it is free from its plastic cladding 8 along contact with the PTFE part 7. For reasons of mechanical stability, PTFE part 7 is held in a metal connector base 9. Fiber 6 projects up to mechanical reference surface 10 of connector base 9. The possibility of an ablation-caused deposit on fiber end surface 11 is reduced here to a minimum by recess 12 in PTFE holder 7.

Figure 5:
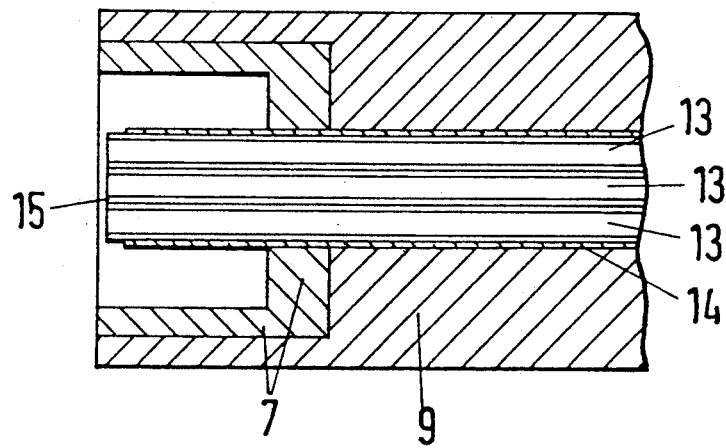
FIG. 5 is a diagrammatic longitudinal section through a launch connector, in which a fiber bundle, held together by a PTFE heat-shrinkable sleeve, is formed in a PTFE part, which, for its part, is enclosed in a metal sleeve.

With use of launch connectors of multifiber ring catheters, as shown in FIG. 5, individual fibers 13 are advantageously retained in hexagonally closest packing by a PTFE heat-shrinkable sleeve 14. On the launch side, fibers 13 are held together with the heat-shrinkable sleeve 14 again in a bore of a PTFE fitting part 7, which is retained in a connector base housing 9. The heat-shrinkable sleeve ends in spaced relation with respect to launch surface 15 of fiber bundle 13.

Without further elaboration, it is believed that one skilled in the art can, using the preceding description, utilize the present invention to its fullest extent. The following preferred specific embodiments, therefore, are to be construed as merely illustrative and limitative of the remainder of the disclosure in any way whatsoever.

The entire texts of all applications, patents, and disclosures, if any, cited above and below, and of corresponding German Utility Application No. G 89 03 333.7, filed Mar. 17, 1989, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An arrangement for protecting the launch end surfaces of laser catheters fed with sweeping, short-pulsed laser light comprising:
   light guide means formed of individual optical fibers configured at the launch end in hexagonally closest packing;
   ablation-resistant means comprising a layer of short fiber pieces on the outside of the light guides means which are not used for laser light transmission, the ablation means being positioned on the surface of the device directly adjacent to the outer periphery of the launch end to shield side portions of the light guides from sweeping laser light, and
   means for connecting the individual fibers and the ablation-resistant means to one another.

2. An arrangement for protecting the launch end surfaces of laser catheters fed with sweeping, short-pulsed laser light comprising:
   light guide means formed of individual optical fibers having distal and proximal ends configured at the launch end in hexagonally closest packing, the optical fibers being held at the proximal ends thereof by a PTFE part with a frictional connection;
   ablation-resistant means positioned on a peripheral surface of the device directly adjacent to the outer periphery of the launch end to shield side portions of the light guides from sweeping laser light; and
   means for connecting the individual fibers and the ablation-resistant means to one another.

3. The device according to claim 2, wherein the PTFE part (7) holding the optical fiber is positioned in a metal connector device (9) with the end surface (11, 15) exposed.

4. An arrangement for protecting the launch end surface of laser catheters fed with sweeping, short-pulsed laser light comprising:
   light guide means formed of individual optical fibers configured at the launch end in hexagonally closest packing;
   ablation-resistant means positioned on the surface of the device directly adjacent to the outer periphery of the launch end to shield side portions of the light guides from sweeping laser light, and
   means for connecting the individual fibers and the ablation-resistant means to one another, the connecting means comprising a PTFE heat-shrinkable sleeve holding the fiber bundle together in hexagonally closest packing by a friction connection and wherein the packing is retained in a PTFE ring.

5. The device of claim 4, wherein the PTFE heat-shrinkable sleeve (14) terminates with an end in spaced relation with respect to the end of the optical fiber.

6. The device of claim 4, wherein some fibers are active and some fibers are inactive and wherein, to protect the fibers which are active, the fiber elements are encased with the heat-shrinkable sleeve, with short fiber pieces extending to the end of the light guide means.

7. An arrangement for protecting the launch end surfaces of laser catheters fed with sweeping, short-pulsed laser light comprising:

light guide means formed of individual optical fibers configured at the launch end in hexagonally closest packing, ablation-resistant means made of polytetrafluoroethylene positioned on a peripheral surface of the device directly adjacent to the outer periphery of the launch end to shield side portions of the light guides from sweeping laser light, and means for connecting the individual fibers and the ablation-resistant means to one another.

8. A process for protecting side portions adjacent front end launch surfaces of a laser catheter made of fiber bundles of individual optical fibers, the bundles being sheathed with plastic cladding and fed with sweeping, short-pulsed laser light for the photoablation of deposits in the vessel system of the human body, the process comprising:

attaining as high a coupling efficiency as possible by freeing individual optical fibers of the laser catheter from the plastic cladding on the launch side portions and placing the fibers in hexagonally closest packing, applying ablation-resistant means to the outer circumference of the fiber bundle to protect the surface of the launch device adjacent the launch side portion from photoablation by the sweeping short-pulsed laser light, and joining the individual fibers and the ablation-resistant means to one another.

9. The process of claim 8, wherein a thin tube of the same material as the optical fibers is fused over the hexagonally closest packed individual fibers and further including the step of polishing launch surfaces.

10. The process of claim 8, including the step of shrinking a sleeve of heat shrinkable material over the hexagonally closest packing of the fiber bundle and retaining the packing in a metal holder having a front side thereon, and then covering the front side of the metal holder with a layer of material selected from the group consisting of polymethylsiloxane and silicate.

11. The process of claim 8, including imbedding the hexagonally closest packing of the fiber bundle in a material bed disposed in a metal sleeve with the fiber bundle having a portion projecting therefrom wherein the material bed is a silicate material and spacing the projecting portion of the fiber bundle adjacent an end of the metal sleeve proximate the front end launch surface and then optically polishing the front end launch surfaces of the bundle.

12. The process of claim 8, including embedding the hexagonally closest packing of the fiber bundle by friction connection within at least one layer of a PTFE heat-shrinkable sleeve and then surrounding the fiber bundle in a PTFE which PTFE is anchored by friction in a connector base.

13. The process of claim 12, wherein the PTFE heat-shrinkable sleeve terminates a short distance before the fiber bundle end surface terminates.

14. The process of claim 12, wherein as a result of shrinking between the fiber bundle and the heat-shrinkable sleeve an outside layer of fiber pieces is exposed and further including the step of applying the heat-shrinkable sleeve up to the fiber bundle end and then optically polishing the end of the fiber bundle.

* * * * *